(12) United States Patent
Yang et al.

(10) Patent No.: US 11,213,820 B2
(45) Date of Patent: Jan. 4, 2022

(54) MICROFLUIDIC CHIP, DEVICE AND METHOD FOR CHEMILUMINESCENCE IMMUNOASSAY

(71) Applicants: Beijing BOE Display Technology Co., Ltd., Beijing (CN); BOE Technology Group Co., Ltd., Beijing (CN)

(72) Inventors: Zhaokun Yang, Beijing (CN); Yun Qiu, Beijing (CN); Sha Liu, Beijing (CN); Xiao Sun, Beijing (CN)

(73) Assignees: BEIJING BOE DISPLAY TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 521 days.

(21) Appl. No.: 16/080,179

(22) PCT Filed: Jan. 22, 2018

(86) PCT No.: PCT/CN2018/073606
§ 371 (c)(1),
(2) Date: Aug. 27, 2018

(87) PCT Pub. No.: WO2019/007036
PCT Pub. Date: Jan. 10, 2019

(65) Prior Publication Data
US 2020/0330986 A1    Oct. 22, 2020

(30) Foreign Application Priority Data
Jul. 5, 2017    (CN) .......................... 201710542327.5

(51) Int. Cl.
*B01L 3/00*    (2006.01)
*G01N 21/76*    (2006.01)
*G01N 33/542*    (2006.01)

(52) U.S. Cl.
CPC ....... *B01L 3/502715* (2013.01); *B01L 3/5027* (2013.01); *G01N 21/76* (2013.01);
(Continued)

(58) Field of Classification Search
CPC ........... B01L 3/502715; B01L 2200/10; B01L 2300/0861; B01L 3/00; B01L 3/5027;
(Continued)

(56) References Cited

U.S. PATENT DOCUMENTS 6,727,479 B2 *   4/2004   Villa .................... B01J 19/0093
                                               219/201
7,745,207 B2 *   6/2010   Jovanovich .......... C12Q 1/6869
                                               435/288.5

(Continued)

FOREIGN PATENT DOCUMENTS

WO    2007033385 A2    3/2007

OTHER PUBLICATIONS

K. Tsukagoshi, et al., "Development of a Micro Total Analysis System Incorporating Chemiluminescence Detection and Application to Detection of Cancer Markers," Feb. 2005, Anal. Chem., 77, 6, 1684-1688 (Year: 2005).*

(Continued)

*Primary Examiner* — Samuel P Siefke
*Assistant Examiner* — Henry H Nguyen
(74) *Attorney, Agent, or Firm* — Myers Bigel, P.A.

(57) ABSTRACT

The present disclosure provides a microfluidic chip, a device and a method for chemiluminescence immunoassay. The microfluidic chip includes a base plate, as well as a first liquid inlet channel, a second liquid inlet channel, a third liquid inlet channel, an immune reaction cell, and a luminescent reaction cell formed on a first surface of the base plate. An outlet end of the immune reaction cell is in communication with a liquid inlet end of the luminescent
(Continued)

reaction cell, and a primer is disposed in the immune reaction cell for immobilizing an antigen-antibody complex generated in the immune reaction cell.

15 Claims, 3 Drawing Sheets

(52) U.S. Cl.
CPC ........ *G01N 33/542* (2013.01); *B01L 2200/10* (2013.01); *B01L 2300/0861* (2013.01); *B01L 2300/0867* (2013.01); *B01L 2300/0883* (2013.01)

(58) Field of Classification Search
CPC ..... B01L 2300/0867; B01L 2300/0883; B01L 2400/0487; B01L 2300/1827; B01L 2300/0816; G01N 21/76; G01N 33/542; G01N 2458/10; G01N 33/54366
See application file for complete search history.

(56) References Cited

U.S. PATENT DOCUMENTS

| | | | |
|---|---|---|---|
| 9,463,460 B2* | 10/2016 | Kumaran | B01F 13/0059 |
| 2002/0187564 A1* | 12/2002 | Chow | B01L 3/5027 506/39 |
| 2003/0017467 A1* | 1/2003 | Hooper | B01J 19/0046 435/6.11 |
| 2004/0072278 A1* | 4/2004 | Chou | G01N 15/1456 435/29 |
| 2005/0221281 A1 | 10/2005 | Ho | |
| 2007/0074972 A1 | 4/2007 | Nassef et al. | |
| 2007/0172389 A1 | 7/2007 | Wilding et al. | |
| 2010/0158756 A1* | 6/2010 | Taylor | B01L 3/527 422/69 |
| 2010/0202968 A1 | 8/2010 | Nitsch et al. | |
| 2014/0080729 A1* | 3/2014 | Grego | G01N 33/54373 506/9 |
| 2015/0111306 A1* | 4/2015 | Lee | C12N 15/115 436/501 |
| 2015/0232942 A1* | 8/2015 | Abate | B01L 3/502784 506/9 |
| 2017/0259266 A1* | 9/2017 | Yamawaki | B01F 13/0079 |

OTHER PUBLICATIONS

Ching-Chu Wu, et al., "Measurement of glycated hemoglobin levels using an integrated microfluidic system," Mar. 2014, Microfluid Nanofluid, 18:613-621. (Year: 2014).*

Tsukagoshi, et al., "Development of a Micro Total Analysis System Incorporating Chemiluminescence Detection and Application to Detection of Cancer Markers," Feb. 2005, Anal. Chem., 77, 6, 1684-1688. (Year: 2005).*

Xu et al., "Microchip-based cellular biochemical systems for practical applications and fundamental research: from microfluidics to nanofluidics", Aug. 2011, Anal Bioanal Chem, 402:99-107. (Year: 2011).*

Lee et al., "A polymer lab-on-a-chip for reverse transcription (RT)-PCR based point-of-care clinical diagnostics", Oct. 2008, Lab on a Chip,8, 2121-2127 (Year: 2008).*

"Communication with Supplementary European Search Report", EP Application No. 18755121.3, dated Feb. 19, 2021, 7 pp.

"Examination report under sections 12 & 13 of the Patents Act, 1970 and the Patents Rules, 2003", IN Patent Application No. 201847032661, dated Feb. 28, 2021, 4 pp.

* cited by examiner

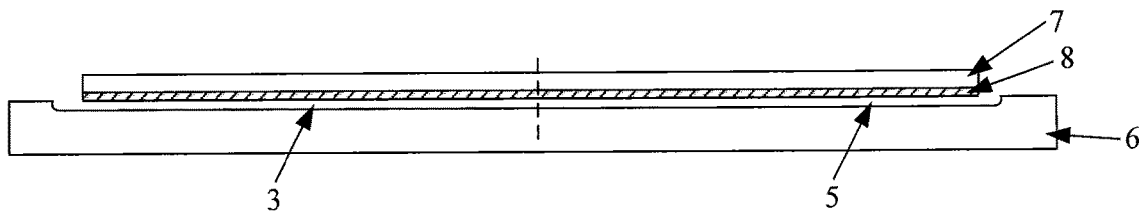

Fig. 3

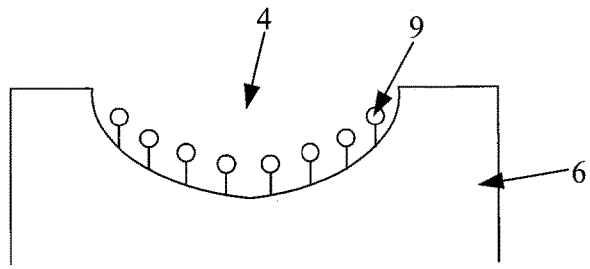

Fig. 4

| injecting an antigen to be tested and an antibody into an immune reaction cell through a first liquid inlet channel, such that an immune reaction happens between the antigen to be tested and the antibody, thereby generating an antigen-antibody complex | — S1 |

| injecting an alkaline solution into the immune reaction cell through a second liquid inlet channel, such that double strands unwind between the DNA-labeled antibody and the primer, thereby the antigen-double antibody complex and the alkaline solution flowing into a luminescent reaction cell | — S2 |

| injecting an oxidant solution into the luminescent reaction cell through a third liquid inlet channel, such that the acridinium ester decomposes to emit light under influences of the oxidant solution and the alkaline solution | — S3 |

Fig. 5

MICROFLUIDIC CHIP, DEVICE AND METHOD FOR CHEMILUMINESCENCE IMMUNOASSAY

CROSS REFERENCE TO RELATED APPLICATIONS

The present application is a 35 U.S.C. 371 national stage application of PCT International Application No. PCT/CN2018/073606, filed on Jan. 22, 2018 which claims the benefit of Chinese Patent Application No. 201710542327.5, filed on Jul. 5, 2017, the contents of both of which are incorporated herein by reference in their entireties.

TECHNICAL FIELD

The present disclosure relates to the field of medical technology, in particular to a microfluidic chip, a device and a method for chemiluminescence immunoassay.

BACKGROUND

At present, immunodiagnosis is mainly performed by a chemiluminescence immunoassay analyzer. The existing instrument includes an immunoreaction device and a chemiluminescence analyzer. In the immunoreaction device of this instrument, a conventional test tube is used as a reaction vessel, and the separation between the reaction product and the reagent is realized by the micro-bead technology, which requires a large amount of test reagents and magnetic beads. In addition, since the test tube is used as a reaction vessel, the amount of reagents required is large and the cost is high.

In addition, the existing chemiluminescence immunoassay analyzers are large in size and inconvenient to store.

SUMMARY

According to an aspect of the present disclosure, a microfluidic chip for chemiluminescence immunoassay is provided. The microfluidic chip includes a base plate, as well as a first liquid inlet channel, a second liquid inlet channel, a third liquid inlet channel, an immune reaction cell, and a luminescent reaction cell formed on a first surface of the base plate. An outlet end of the immune reaction cell is in communication with a liquid inlet end of the luminescent reaction cell, and a primer is disposed in the immune reaction cell for immobilizing an antigen-antibody complex generated in the immune reaction cell. A liquid outlet end of the first liquid inlet channel is in communication with a liquid inlet end of the immune reaction cell, and the first liquid inlet channel is used to introduce an antigen to be tested and an antibody into the immune reaction cell. A liquid outlet end of the second liquid inlet channel is in communication with the liquid inlet end of the immune reaction cell, and the second liquid inlet channel is used to introduce an alkaline solution into the immune reaction cell. A liquid outlet end of the third liquid inlet channel is in communication with the liquid inlet end of the luminescent reaction cell, and the third liquid inlet channel is used to introduce an oxidant solution into the luminescent reaction cell.

Optionally, the microfluidic chip for chemiluminescence immunoassay further includes: a cover plate disposed on a second surface of the base plate, wherein the second surface is opposite to the first surface, and the base plate includes a reserved area and a non-reserved area. The first liquid inlet channel, the second liquid inlet channel, the third liquid inlet channel, the immune reaction cell and the luminescent reaction cell are all located in the non-reserved area. The cover plate covers the non-reserved area. The liquid inlet ends of the first liquid inlet channel, the second liquid inlet channel, and the third liquid inlet channel extend into the reserved area.

Optionally, the microfluidic chip for chemiluminescence immunoassay further includes: a heating electrode disposed on a side of the cover plate adjacent to the base plate, wherein an orthographic projection of the heating electrode on the base plate at least covers the immune reaction cell.

Optionally, in the microfluidic chip for chemiluminescence immunoassay as proposed above, liquid pumps are disposed at the liquid inlet ends of the first liquid inlet channel, the second liquid inlet channel, and the third liquid inlet channel, wherein the liquid pumps are used to deliver corresponding liquids to each of the liquid inlet ends.

Optionally, in the microfluidic chip for chemiluminescence immunoassay as proposed above, the base plate and the cover plate are connected by a bonding process Optionally, in the microfluidic chip for chemiluminescence immunoassay as proposed above, the first liquid inlet channel includes: a first sub-channel, a second sub-channel, and a third sub-channel. Liquid outlet ends of the first sub-channel, the second sub-channel, and the third sub-channel are concentrated at a first node, wherein the first node is in communication with the liquid inlet end of the immune reaction cell through a connection sub-channel. The first sub-channel, the second sub-channel, and the third sub-channel are used to introduce an antigen to be tested, a first antibody, and a second antibody into the immune reaction cell respectively.

Optionally, in the microfluidic chip for chemiluminescence immunoassay as proposed above, the first antibody is a DNA-labeled antibody, and the second antibody is an acridinium ester-labeled antibody.

Optionally, in the microfluidic chip for chemiluminescence immunoassay as proposed above, the first liquid inlet channel further includes: a fourth sub-channel. A liquid outlet end of the fourth sub-channel is in communication with the connection sub-channel, and the fourth sub-channel is used to introduce a cleaning solution into the immune reaction cell.

Optionally, in the microfluidic chip for chemiluminescence immunoassay as proposed above, the immune reaction cell comprises a fifth sub-channel and the fifth sub-channel comprises one or more segments that are parallel to each other and connected end to end. The luminescent reaction cell comprises a sixth sub-channel and the sixth sub-channel comprises one or more segments that are parallel to each other and connected end to end. Optionally, at least one of the fifth sub-channel and the sixth sub-channel has a linear shape.

Optionally, in the microfluidic chip for chemiluminescence immunoassay as proposed above, a length of the fifth sub-channel is L1, and a length of the sixth sub-channel is L2, wherein $2 \times L1 < L2$.

Optionally, in the microfluidic chip for chemiluminescence immunoassay as proposed above, cross-sectional shapes of each of the sub-channels (including the first sub-channel, the second sub-channel, the third sub-channel, the fourth sub-channel, the fifth sub-channel, and the sixth sub-channel), the second liquid inlet channel, and the third liquid inlet channel are all semi-circular.

Optionally, in a specific example of the above embodiment, a diameter of the semi-circular cross section ranges from 1 um to 20 um.

According to another aspect of the present disclosure, a device for chemiluminescence immunoassay is also provided. The device includes the microfluidic chip as described in any of the above embodiments.

According to yet another aspect of the present disclosure, a method for chemiluminescence immunoassay is further provided. The method is based on the microfluidic chip as described in any of the above embodiments, and includes the steps of: injecting an antigen to be tested and an antibody into the immune reaction cell through a first liquid inlet channel, such that an antigen-antibody complex is generated by an immune reaction between the antigen to be tested and the antibody, the antigen-antibody complex being immobilized on a primer in the immune reaction cell; injecting an alkaline solution into the immune reaction cell through a second liquid inlet channel, such that double strands unwind between the antigen-antibody complex and the primer, thereby the antigen-antibody complex and the alkaline solution flowing into a luminescent reaction cell; and injecting an oxidant solution into the luminescent reaction cell through a third liquid inlet channel, such that the antigen-antibody complex decomposes to emit light under influences of the oxidant solution and the alkaline solution, wherein emitted photons can be detected by a photon counter located below the microfluidic chip.

Optionally, in a specific embodiment, the first liquid inlet channel of the microfluidic chip includes a fourth sub-channel, wherein a liquid outlet end of the fourth sub-channel is in communication with a liquid inlet end of the immune reaction cell through a connection sub-channel. In such a case, the method for chemiluminescence immunoassay further includes the step of: injecting a cleaning solution into the immune reaction cell through the fourth sub-channel, before injecting the alkaline solution into the immune reaction cell through the second liquid inlet channel, such that the antigen to be tested and the antibody, which are not reacted in the connection sub-channel and the immune reaction cell, are washed out from a liquid outlet end of the immune reaction cell.

BRIEF DESCRIPTION OF THE DRAWINGS

FIG. 2 is a schematic cross-sectional view taken along the line A-A in FIG. 1a;

FIG. 3 is a schematic cross-sectional view taken along the line B-B in FIG. 1a;

FIG. 4 is a schematic cross-sectional view of an immune reaction cell in a microfluidic chip according to an embodiment of the present disclosure;

FIG. 5 is a flow chart of a method for chemiluminescence immunoassay according to an embodiment of the present disclosure.

DETAILED DESCRIPTION OF THE EMBODIMENTS

To enable those skilled in the art to understand technical solutions of the present disclosure in a better way, a microfluidic chip, a device and a method for chemiluminescence immunoassay provided by the present disclosure will be described in detail below with reference to the drawings.

Figure 1A:
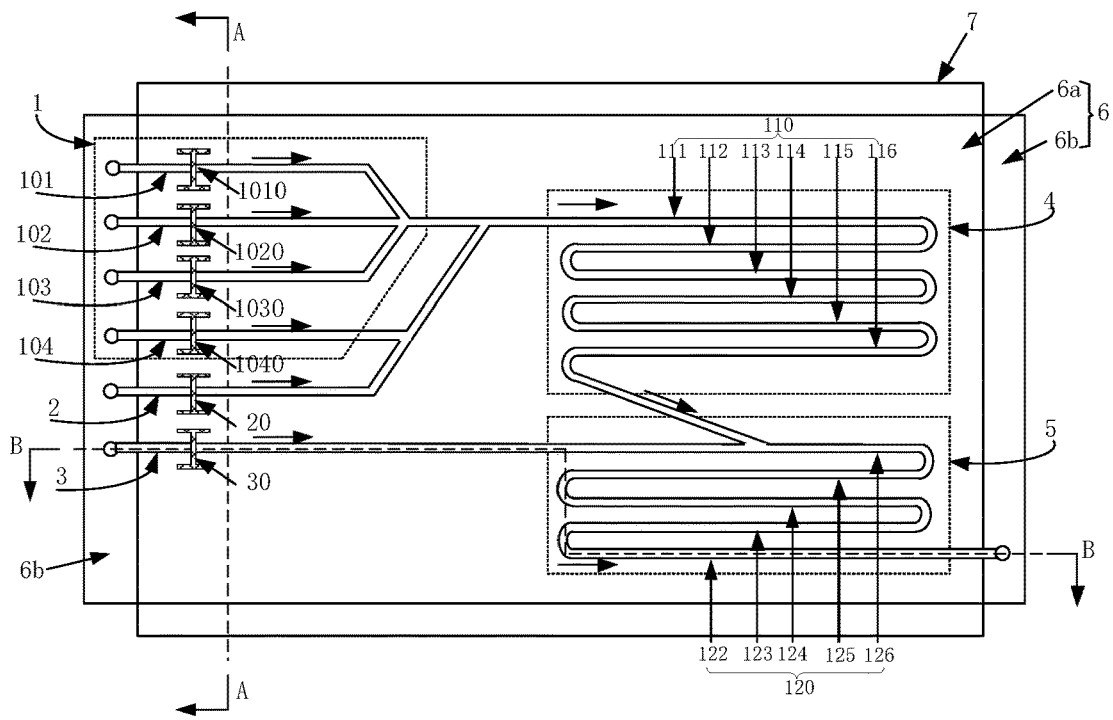
FIG. 1a is a top view of a microfluidic chip according to an embodiment of the present disclosure.

FIG. 1a is a top view of a microfluidic chip according to an embodiment of the present disclosure. FIG. 2 is a cross-sectional view taken along the line A-A in FIG. 1a. FIG. 3 is a cross-sectional view taken along the line B-B in FIG. 1a. FIG. 4 is a schematic cross-sectional view of an immune reaction cell in a microfluidic chip according to an embodiment of the present disclosure. As shown in FIG. 1a to FIG. 4, the microfluidic chip can be used for chemiluminescence immunoassay, and the microfluidic chip includes: a base plate 6, as well as a first liquid inlet channel 1, a second liquid inlet channel 2, third liquid inlet channel 3, immune reaction cell 4, and luminescent reaction cell 5 formed on a first surface of the base plate 6.

An outlet end of the immune reaction cell 4 is in communication with a liquid inlet end of the luminescent reaction cell 5, and a primer 9 (such as a small segment of single-stranded DNA or RNA) is disposed in the immune reaction cell 4 for immobilizing an antigen-antibody complex generated in the immune reaction cell 4. As an example, one end of the primer 9 is fixed to a wall of the immune reaction cell 4 by a surface modification technique.

A liquid outlet end of the first liquid inlet channel 1 is in communication with a liquid inlet end of the immune reaction cell 4, and the first liquid inlet channel 1 is used to introduce an antigen to be tested and two antibodies into the immune reaction cell 4.

A liquid outlet end of the second liquid inlet channel 2 is in communication with the liquid inlet end of the immune reaction cell 4, and the second liquid inlet channel 2 is used to introduce an alkaline solution into the immune reaction cell 4.

A liquid outlet end of the third liquid inlet channel 3 is in communication with the liquid inlet end of the luminescent reaction cell 5, and the third liquid inlet channel 3 is used to introduce an oxidant solution into the luminescent reaction cell 5.

The immune reaction cell 4 is used for the immune reaction (in which the antibody and the antigen specifically combine) between the antigen to be tested and the antibody, so as to generate the antigen-antibody complex. In this embodiment, a dual antibody sandwiched approach is employed in which the antibody includes two types. Specifically, the two types of antibodies include a DNA-labeled antibody and an acridinium ester-labeled antibody. In this case, the product in the immune reaction cell 4 is an antigen-dual antibody complex.

The luminescent reaction cell 5 is used for the luminescence reaction of the antigen-dual antibody complex under influences of an oxidant and a weak alkaline environment. In such a case, the emitted photons can be detected by a photon counter located below the microfluidic chip for analysis of the amount of antigen to be tested.

In the present disclosure, an etching process (e.g., a chemical etching process, a laser etching process) can be performed on a surface of a base plate 6, so as to form a first liquid inlet channel 1, a second liquid inlet channel 2, a third liquid inlet channel 3, an immune reaction cell 4 and a luminescent reaction cell 5.

In the present disclosure, a microfluidic chip is used to perform a series of processes, such as injection, mixing, reaction, and detection, in the chemiluminescence immunoassay. Compared to the case where a conventional test tube is used as a reaction vessel in a conventional scheme, the technical solution proposed in the present disclosure can greatly reduce the amount of reagents used in the analysis process and reduce the analysis cost. In addition, the microfluidic chip is small in size, light in weight, and convenient to store.

In an embodiment, optionally, the microfluidic chip further includes: a cover plate 7 disposed on a second surface of the base plate 6, wherein the second surface is opposite to the first surface on which the liquid inlet channels and the reaction cells are disposed. The base plate 6 is further divided into a reserved area 6b and a non-reserved area 6a. Each of the liquid inlet channels and the two reaction cells is located in the non-reserved area 6a, and the cover plate 7 covers the non-reserved area 6a. Further, the liquid inlet ends of the first liquid inlet channel 1, the second liquid inlet channel 2, and the third liquid inlet channel 3 extend into the reserved area 6b. By providing the cover plate, it may effectively prevent the liquid in each of the liquid inlet channels and the reaction cells from overflowing.

It should be noted that, in the drawings, the reserved area 6b is shown as being located at two peripheral areas of the non-reserved area 6a opposite to each other, but this is merely an example and does not impose any limitation on the technical solution of the present disclosure.

In an embodiment, optionally, materials suitable for the base plate 6 and the cover plate 7 are both glass. In this case, the base plate 6 and the cover plate 7 can be connected by a glass-to-glass bonding process. Thus, there is no need to use an adhesive or a fixed structure.

The specific process for implementing chemiluminescence immunoassay using the microfluidic chip as provided by the present disclosure will be described in detail below.

First, an antigen to be tested, a DNA-labeled antibody, and an acridinium ester-labeled antibody are injected into the immune reaction cell 4 through the first liquid inlet channel 1. An antigen-dual antibody complex is generated by an immune reaction between these three in the immune reaction cell 4.

In an embodiment, the antigen to be tested, the DNA-labeled antibody, and the acridinium ester-labeled antibody may be mixed first, and then the mixed solution is injected into the immune reaction cell 4 through the first liquid inlet channel 1.

If the method of mixing first and then injection is employed, a large amount of reagents will be required in the pre-mixing process. In order to solve this problem, in an embodiment, optionally, the first liquid inlet channel 1 includes: a first sub-channel 101, a second sub-channel 102, and a third sub-channel 103. The liquid inlet ends of the first sub-channel 101, the second sub-channel 102, and the third sub-channel 103 extend independently into a reserved area, respectively. The liquid outlet ends of the first sub-channel 101, the second sub-channel 102, and the third sub-channel 103 are concentrated at a first node, wherein the first node is in communication with a liquid inlet end of the immune reaction cell 4 through a connection sub-channel. The first sub-channel 101, the second sub-channel 102, and the third sub-channel 103 are used to introduce the antigen to be tested, the DNA-labeled antibody (first antibody), and the acridinium ester-labeled antibody (second antibody) into the immune reaction cell 4, respectively.

In an embodiment, three independent sub-channels are provided for injecting the antigen to be tested and the two antibodies, respectively, thereby achieving injection first and then mixing, and greatly reducing the amount of reagents. In addition, since the antigen to be tested and the two antibodies are injected through separate sub-channels, the amount of antigen to be tested and the amount of two antibodies can be individually controlled.

Optionally, liquid pumps 1010, 1020, 1030, 1040 are disposed at the liquid inlet ends of the first liquid inlet channel 1 (including the first sub-channel 101, the second sub-channel 102, and the third sub-channel 103). In this way, precise control over the amount of injected reagents can be achieved by delivering corresponding liquids to the liquid inlet ends of the first liquid inlet channel through the liquid pumps 1010, 1020, 1030, 1040.

Optionally, the cross-sectional shapes of the first sub-channel 101, the second sub-channel 102, and the third sub-channel 103 are semi-circular, and diameters of the first sub-channel 101, the second sub-channel 102, and the third sub-channel 103 range from 1 um to 20 um.

Optionally, a heating electrode 8 is disposed on a side of the cover plate 7 facing the base plate 6, and the heating electrode 8 covers at least an area corresponding to the immune reaction cell 4. By applying a certain current to the heating electrode 8 such that heat is generated by the heating electrode 8, it is ensured that the ambient temperature of the immune reaction cell 4 is at a preset value (generally 37° C.). Thus, the immune reaction between the antigen to be tested and the two antibodies in the immune reaction cell 4 is promoted. Optionally, materials suitable for the heating electrode 8 include at least one of gold, silver, and aluminum. The heating electrode 8 can be formed on a surface of the cover plate 7 by sputtering or plating.

It should be noted that when the heating electrode 8 made of metal material is disposed on the side of the cover plate 7 facing the base plate 6, the base plate 6 and the cover plate 7 can be connected by a metal-glass bonding process.

In addition, in the drawings, the heating electrode 8 is illustrated as covering the entire cover plate 7, but this is only an exemplary solution. In this way, the temperature of the entire microfluidic chip can be made to be at a preset value, thereby being more favorable for maintaining a stable temperature of the immune reaction cell 4.

After generating an antigen-dual antibody complex by the immune reaction between the antigen to be tested, the DNA-labeled antibody and the acridinium ester-labeled antibody, the DNA-labeled antibody in the antigen-dual antibody complex will be complementary to and combined with a primer 9 in the immune reaction cell 4, so as to form a double-stranded structure. In this way, the antigen-dual antibody complex will be immobilized on the primer 9.

It should be noted that the time duration of the immune reaction can be adjusted according to actual requirements. For example, when performing a rapid test, the time duration of the immune reaction can be set to be about 10 minutes. Instead, when performing a normal test, the time duration of the immune reaction can be set to be about 30 minutes.

Optionally, the immune reaction cell 4 includes a fifth sub-channel 110 and the fifth sub-channel 110 comprises one or more segments 111, 112, 113, 114, 115, 116 that are parallel to each other and connected end to end. When there is a plurality of fifth sub-channels, all the fifth sub-channels are connected end to end. In this case, the volume of the immune reaction cell 4 is small, and the amount of reagents required is also small accordingly. Optionally, the cross-sectional shape of the fifth sub-channel is semi-circular, and a diameter of the fifth sub-channel ranges from 1 um to 20 um.

After that, an alkaline solution is injected into the immune reaction cell 4 through the second liquid inlet channel 2, so that double strands unwind between the DNA-labeled antibody and the primer 9, thereby the antigen-dual antibody complex and the alkaline solution flowing into the luminescent reaction cell 5. In a specific example, the alkaline solution is a sodium hydroxide solution. Optionally, the cross-sectional shape of the second liquid inlet channel 2 is semi-circular, and a diameter of the second liquid inlet channel 2 ranges from 1 um to 20 um.

Optionally, a liquid pump 20 is disposed at a liquid inlet end of the second liquid inlet channel 2. In this way, precise control over the amount of the injected alkaline solution can be achieved by delivering the alkaline solution to the liquid inlet end of the second liquid inlet channel through the liquid pump 20.

In an embodiment, the antigen to be tested and the antibodies, which are not subjected to an immune reaction, are inevitably present in the immune reaction cell 4. Such unreacted antigen to be tested and antibodies affect the detection result of the luminescence reaction after entering the luminescent reaction cell 5. In order to solve this problem, in an embodiment, optionally, the first liquid inlet channel 1 further includes a fourth sub-channel 104. A liquid inlet end of the fourth sub-channel 104 extends to the reserved area. A liquid outlet end of the fourth sub-channel 104 is in communication with the connection sub-channel. The fourth sub-channel 104 is used to introduce a cleaning solution into the immune reaction cell 4, after the end of the immune reaction and before injecting the alkaline solution into the immune reaction cell 4 through the second liquid inlet channel 2. Specifically, the cleaning solution is deionized water.

Optionally, the cross-sectional shape of the fourth sub-channel 104 is semi-circular, and a diameter of the fourth sub-channel 104 ranges from 1 um to 20 um.

When the deionized water is injected into the immune reaction cell 4 through the fourth sub-channel 104, the unreacted antigen to be tested and antibodies in the connection sub-channel and the immune reaction cell 4 will be washed away and be discharged through a waste liquid outlet (i.e., a liquid outlet end of the luminescent reaction cell). In this way, the unreacted antigen to be tested and antibodies can be effectively prevented from entering the luminescent reaction cell 5. In this process, the cleaning time can be adjusted according to actual situations. It should be noted that, when the immune reaction cell 4 is washed with deionized water, since the antigen-dual antibody complex is immobilized on the primer 9, the antigen-dual antibody complex can remain in the immune reaction cell 4, i.e., not being washed away.

Finally, an oxidant solution is injected into the luminescent reaction cell 5 through the third liquid inlet channel 3. Thus, under influences of the oxidant solution and the alkaline solution, the antigen-dual antibody complex, in particular, the antibody-acridinium ester, decomposes and emits light. Specifically, the oxidant solution is a hydrogen peroxide solution.

Optionally, a liquid pump 30 is disposed at the liquid inlet end of the third liquid inlet channel 3. In this way, precise control over the amount of the injected oxidant solution can be achieved by delivering the oxidant solution to the liquid inlet end of the third liquid inlet channel through the liquid pump 30.

Optionally, the cross-sectional shape of the third liquid inlet channel 3 is semi-circular, and a diameter of the third liquid inlet channel 3 ranges from 1 um to 20 um.

Under influences of the oxidant solution and the alkaline solution, the acridinium ester decomposes, and photons can be continuously and stably emitted. The photon energy released by the emitted light is detected and recorded by a photon counter. After that, the intensity of the light energy is converted to the concentration of the antigen to be tested on a standard curve by a computer processing system.

Optionally, the luminescent reaction cell 5 includes a sixth sub-channel 120 and the sixth sub-channel 120 comprises one or more segments 122, 123, 124, 125, 126 that are parallel to each other and connected end to end. When there is a plurality of sixth sub-channels, all the sixth sub-channels are connected end to end. In this case, the volume of the luminescent reaction cell 5 is small, and the amount of reagents required is also small accordingly. Optionally, the cross-sectional shape of the sixth sub-channel is semi-circular, and a diameter of the sixth sub-channel ranges from 1 um to 20 um.

Figure 1B:
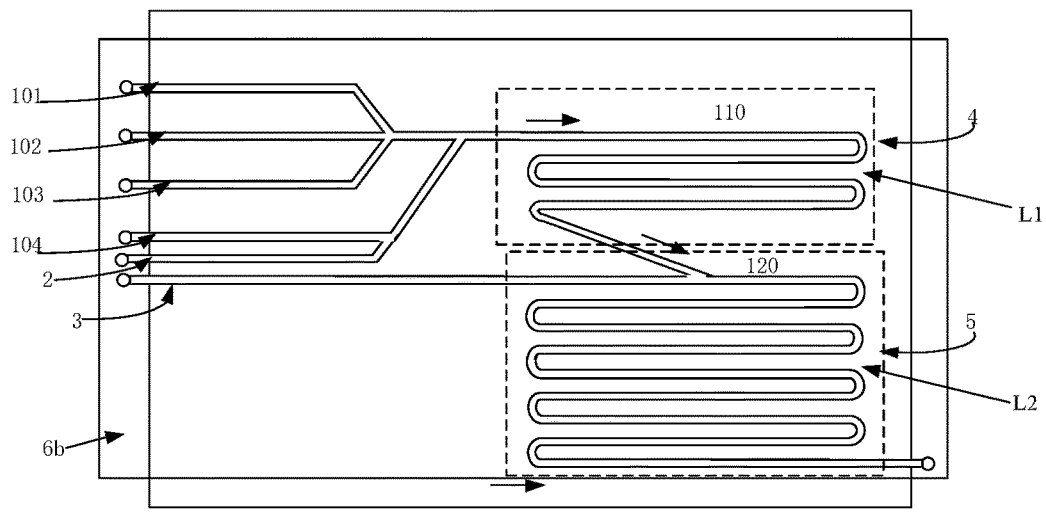
FIG. 1b is a top view of a microfluidic chip according to an embodiment of the present disclosure.
Figure 2:
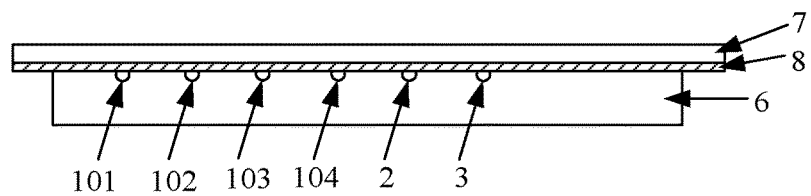

Further optionally, FIG. 1*b* is a top view of a microfluidic chip according to an embodiment of the present disclosure. As shown in FIG. 1*b*, in the case where the cross-sectional area of the fifth sub-channel 110 and the sixth sub-channel 120 is the same, a length of the fifth sub-channel 110 and a length of the sixth sub-channel 120 satisfy the following relationship: 2×L1<L2, where L1 is the length of the fifth sub-channel 110, and L2 is the length of the sixth sub-channel 120. By setting the length of the sixth sub-channel 120 to be more than twice of the length of the fifth sub-channel 110, it is ensured that the product of immune reaction is completely introduced into the luminescent reaction cell, thereby ensuring the accuracy of subsequent detection results.

It should be noted that after the chemiluminescence immunoassay is completed by using the above microfluidic chip, deionized water can be continuously injected into the first sub-channel 101 to clean the first sub-channel 101, the connection sub-channel, the immune reaction cell 4, and the luminescent reaction cell 5. Thus, the cleaned microfluidic chip can be reused.

In addition, in the above descriptions, as an example, the cross-sectional shapes of each of the sub-channels and channels are shown as a semi-circle, but this is only an exemplary case, which does not impose any limitation on the technical solution of the present disclosure. In the present disclosure, the cross-sectional shapes of each of the sub-channels and channels can also be other shapes, which are not exemplified herein.

According to another aspect of the present disclosure, a device for chemiluminescence immunoassay is also provided. The device includes: the microfluidic chip as described in any of the above embodiments. The device adopts the microfluidic chip as provided in the above embodiments. For details, refer to the corresponding content in the above embodiments, and details are not described herein again.

FIG. 5 is a flow chart of a method for chemiluminescence immunoassay according to an embodiment of the present disclosure. As shown in FIG. 5, the method for chemiluminescence immunoassay is based on the microfluidic chip as described in any of the above embodiments, and specifically includes the following steps.

In step S1, an antigen to be tested and an antibody are injected into an immune reaction cell through a first liquid inlet channel, such that an immune reaction happens between the antigen to be tested and the antibody, thereby generating an antigen-antibody complex.

In an embodiment, a dual antibody sandwiched approach is employed in which two antibodies are injected into the immune reaction cell through the first liquid inlet channel, and the two antibodies are a DNA-labeled antibody and an acridinium ester-labeled antibody, respectively.

In step S1, the antigen to be tested and the two antibodies may be mixed first, and then the mixture is injected into the immune reaction cell through the first liquid inlet channel. Alternatively, the antigen to be tested and the two antibodies may first be injected into the immune reaction cell through three separate sub-channels (i.e., a first sub-channel, a second sub-channel, and a third sub-channel), and then the three are mixed in an immune reaction cell.

In the immune reaction cell, the DNA-labeled antibody in the antigen-dual antibody complex generated by the immune reaction is immobilized on a primer in the immune reaction cell.

Optionally, a heating electrode can also be disposed on a side of the cover plate facing the base plate. The heating electrode allows the ambient temperature of the immune reaction cell at a preset value (generally 37° C.), thereby effectively promoting the immune reaction between the antigen to be tested and the two antibodies in the immune reaction cell.

In step S2, an alkaline solution is injected into the immune reaction cell through a second liquid inlet channel such that double strands unwind between the DNA-labeled antibody and the primer, thereby the antigen-dual antibody complex and the alkaline solution flowing into the luminescent reaction cell.

Optionally, the alkaline solution is a sodium hydroxide solution.

Under influences of the alkaline solution, double strands unwind between the DNA-labeled antibody in the antigen-dual antibody complex and the primer, thereby the antigen-dual antibody complex and the alkaline solution flowing into the luminescent reaction cell.

In step S3, an oxidant solution is injected into the immune reaction cell through a third liquid inlet channel. In this case, the acridinium ester decomposes and emits light under influences of the oxidant solution and the alkaline solution.

Optionally, the oxidant solution is a hydrogen peroxide solution.

In the luminescent reaction cell, the acridinium ester in the antigen-dual antibody complex decomposes and emits light under influences of the oxidant solution and the alkaline solution. Thus, the emitted photons can be detected by a photon counter located below the microfluidic chip for subsequent analysis of the content of antigens to be tested.

It should be noted that after performing the chemiluminescence immunoassay using the above microfluidic chip, deionized water may be injected into the first sub-channel to clean the first sub-channel, the first connection sub-channel, the immune reaction cell, and the luminescent reaction cell. The microfluidic chip that is cleaned in this manner can be reused.

Figure 6:
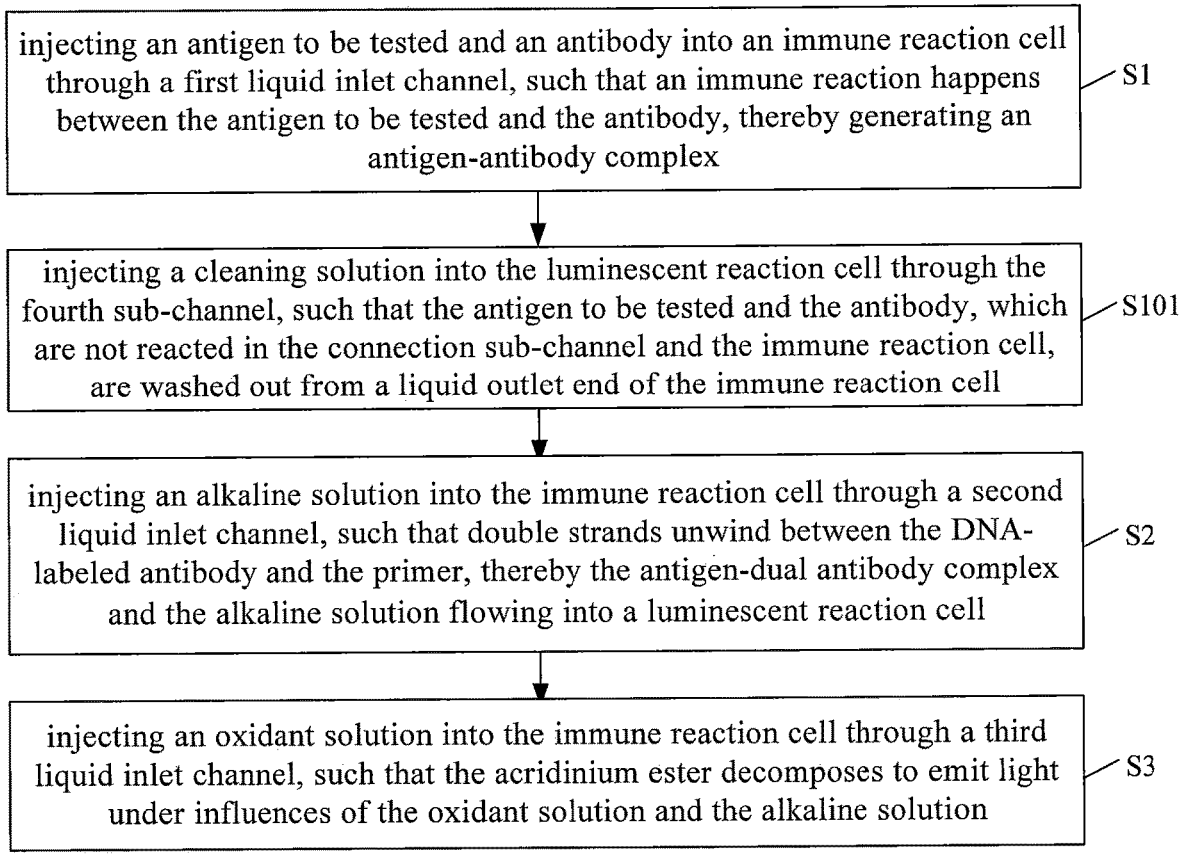
FIG. 6 is a flow chart of a method for chemiluminescence immunoassay according to another embodiment of the present disclosure.

FIG. 6 is a flow chart of a method for chemiluminescence immunoassay according to another embodiment of the present disclosure. As shown in FIG. 6, the method for chemiluminescence immunoassay is based on the microfluidic chip as described above in any of the above embodiments. Moreover, in the microfluidic chip, the first liquid inlet channel includes a fourth sub-channel. In this case, in addition to the step S1 to the step S3 in the above embodiment, the method for chemiluminescence immunoassay further includes an additional step S101 between the step S1 and the step S2. The step S101 will be described in detail below.

In step S101, a cleaning solution is injected into the luminescent reaction cell through the fourth sub-channel, so as to wash away the unreacted antigen to be tested and antibodies in the connection sub-channel and the immune reaction cell through the liquid outlet end of the immune reaction cell.

Optionally, the cleaning solution is deionized water.

After the end of the immune reaction, and before injecting the alkaline solution into the immune reaction cell through the second liquid inlet channel, the fourth sub-channel is used to inject the deionized water into the immune reaction cell. Thus, the unreacted antigen to be tested and antibodies located in the connection sub-channel and the immune reaction cell are washed away and discharged through the waste liquid outlet. In this way, the unreacted antigen to be tested and antibodies can be effectively prevented from entering the luminescent reaction cell, thereby ensuring the accuracy of subsequent detection results.

It should be noted that when the immune reaction cell is washed with deionized water, since the antigen-dual antibody complex is immobilized on the primer, the antigen-dual antibody complex can remain in the immune reaction cell, i.e., not being washed away.

According to the method for chemiluminescence immunoassay provided by an embodiment of the present disclosure, detection of a low amount of reagents can be achieved. It is to be understood that the above embodiments are merely exemplary embodiments employed to illustrate the principle of the present disclosure. However, the present disclosure is not limited to this. Various modifications and improvements can be made by those skilled in the art without departing from the spirit and scope of the present disclosure, and all such modifications and improvements are also considered to fall within the scope of the present disclosure.

The invention claimed is:

1. A microfluidic chip for chemiluminescence immunoassay, comprising:
   a base plate, and
   a first liquid inlet channel, a second liquid inlet channel, a third liquid inlet channel, an immune reaction cell, and a luminescent reaction cell formed on a first surface of the base plate,
   wherein the immune reaction cell comprises a fifth sub-channel and the fifth sub-channel comprises one or more segments that are parallel to each other and connected end to end, and
   wherein the luminescent reaction cell comprises a sixth sub-channel and the sixth sub-channel comprises one or more segments that are parallel to each other and connected end to end,
   wherein an outlet end of the fifth sub-channel is in communication with a liquid inlet end of the sixth sub-channel, and a primer is in the immune reaction cell by fixing one end of the primer to a wall of the immune reaction cell by a surface modification technique,
   wherein a liquid outlet end of the first liquid inlet channel is in communication with a liquid inlet end of the fifth sub-channel,
   wherein a liquid outlet end of the second liquid inlet channel is in communication with the liquid inlet end of the fifth sub-channel,
   wherein a liquid outlet end of the third liquid inlet channel is in communication with the liquid inlet end of the sixth sub-channel,
   wherein the first liquid inlet channel comprises:
   a first sub-channel;
   a second sub-channel; and
   a third sub-channel, wherein a liquid outlet end of the first sub-channel, a liquid outlet end of the second sub-channel, and a liquid outlet end of the third sub-channel are concentrated at a first node, and wherein the first node is in communication with the liquid inlet end of the immune reaction cell through a connection sub-channel, wherein the first liquid inlet channel further comprises: a fourth sub-channel, and wherein a liquid outlet end of the fourth sub-channel is in communication with the connection sub-channel at a second node, wherein the fourth sub-channel and the second liquid inlet channel are concentrated at a third node, and wherein the first node, the second node and the third node are different from each other.

2. The microfluidic chip according to claim 1, further comprising:

a cover plate on a second surface of the base plate, wherein the second surface is opposite to the first surface, wherein the base plate comprises a reserved area and a non-reserved area, wherein the cover plate covers the non-reserved area, wherein the first liquid inlet channel, the second liquid inlet channel, the third liquid inlet channel, the immune reaction cell and the luminescent reaction cell are in the non-reserved area, and wherein a liquid inlet end of the first liquid inlet channel, the second liquid inlet channel, and the third liquid inlet channel extend into the reserved area.

3. The microfluidic chip according to claim 2, further comprising:

a heating electrode on a side of the cover plate adjacent to the base plate, wherein an orthographic projection of the heating electrode on the base plate at least covers the immune reaction cell.

4. The microfluidic chip according to claim 1, wherein a plurality of liquid pumps are at the liquid inlet end of the first liquid inlet channel, the liquid inlet end of the second liquid inlet channel, and the liquid inlet end of the third liquid inlet channel, respectively.

5. The microfluidic chip according to claim 2, wherein the base plate and the cover plate are connected by a bonding process.

6. The microfluidic chip according to claim 1, wherein the first sub-channel is configured to introduce a first antibody into the immune reaction cell, wherein the second sub-channel is configured to introduce a second antibody into the immune reaction cell, and wherein the first antibody comprises a DNA-labeled antibody and the second antibody comprises an acridinium ester-labeled antibody.

7. The microfluidic chip according to claim 6, wherein respective cross-sectional shapes of the first sub-channel, the second sub-channel, the third sub-channel, the second liquid inlet channel, and the third liquid inlet channel are semi-circular.

8. The microfluidic chip according to claim 1, wherein a length of the fifth sub-channel is L1, and a length of the sixth sub-channel is L2, and wherein 2×L1<L2.

9. The microfluidic chip according to claim 8, wherein a cross-sectional shape of the fifth sub-channel and a cross-sectional shape of the sixth sub-channel are semi-circular.

10. The microfluidic chip according to claim 1, wherein cross-sectional shapes of the first sub-channel, the second sub-channel, the third sub-channel, the second liquid inlet channel, and the third liquid inlet channel are semi-circular.

11. The microfluidic chip according to claim 10, wherein diameters of the cross-sectional shapes range from 1 μm to 20 μm.

12. The microfluidic chip according to claim 1, wherein a cross-sectional shape of the fifth sub-channel and a cross-sectional shape of the sixth sub-channel are semi-circular.

13. The microfluidic chip of claim 12, wherein a diameter of the cross-sectional shape of the fifth sub-channel or a diameter of the cross-sectional shape of the sixth sub-channel ranges from 1 μm to 20 μm.

14. The microfluidic chip according to claim 1, wherein respective cross-sectional shapes of the first sub-channel, the second sub-channel, the third sub-channel, the second liquid inlet channel, and the third liquid inlet channel are semi-circular.

15. A device for chemiluminescence immunoassay, comprising:

a microfluidic chip according to claim 1.

* * * * *